United States Patent [19]

Castleman et al.

[11] Patent Number: 4,534,777
[45] Date of Patent: Aug. 13, 1985

[54] GAS SEPARATION APPARATUS

[75] Inventors: Bruce W. Castleman, Kenneth City; David P. McQuire, Dade City; Eugene L. Szonntagh, Largo, all of Fla.

[73] Assignee: Honeywell Inc., Minneapolis, Minn.

[21] Appl. No.: 626,811

[22] Filed: Jun. 29, 1984

[51] Int. Cl.³ .............................................. B01D 53/06
[52] U.S. Cl. ........................................ 55/181; 55/270; 55/390
[58] Field of Search ............... 55/18, 181, 208, 270, 55/387, 389, 59, 62; 250/304, 379, 381, 382, 432 R, 433; 422/83

[56] References Cited

U.S. PATENT DOCUMENTS

| | | | |
|---|---|---|---|
| 2,156,693 | 5/1939 | Jacobson | 422/83 X |
| 2,925,880 | 2/1960 | Munters | 55/390 X |
| 2,993,563 | 7/1961 | Munters et al. | 55/62 X |
| 3,140,936 | 7/1964 | Schwartz | 55/390 X |
| 3,296,773 | 1/1967 | Hemstreet | 55/208 X |
| 3,309,844 | 3/1967 | Hemstreet et al. | 55/208 X |
| 3,568,411 | 3/1971 | Dravnieks et al. | 55/208 |
| 3,590,247 | 6/1971 | Holford | 250/304 X |
| 3,834,125 | 9/1974 | Richter, Jr. | 55/208 |
| 3,940,614 | 2/1976 | Rhodes et al. | 250/432 R X |
| 3,976,450 | 8/1976 | Marcote et al. | 55/270 X |
| 3,982,129 | 9/1976 | Lattin et al. | 250/304 X |
| 4,188,196 | 2/1980 | Casper et al. | 55/270 |
| 4,238,678 | 12/1980 | Castleman et al. | 250/381 |
| 4,242,107 | 12/1980 | Jenkins | 55/208 X |
| 4,421,532 | 12/1983 | Sacchetti et al. | 55/59 X |

Primary Examiner—Robert Spitzer
Attorney, Agent, or Firm—George W. Field

[57] ABSTRACT

In combination: a housing defining separate sorption and desorption chambers; gas analyzing means in communication with the desorption chamber; sorption means mounted for movement between a first condition, in which it is located in the sorption chamber, and a second condition, in which it is located in the desorption chamber; means causing a flow of gas to be analyzed through the sorption chamber when said sorption means is in said first condition; and means causing flow of gas from the desorption chamber to the analyzing means when the sorption means is in the second condition.

4 Claims, 4 Drawing Figures

GAS SEPARATION APPARATUS

FIELD OF THE INVENTION

This invention relates to the field of gas detectors and analyzers, and particularly to such devices having higher sensitivity or specificity than is presently available.

BRIEF OUTLINE OF THE INVENTION

According to the present invention a sorption-desorption device is arranged to be displaced between two positions. In the first position it is in the flow of gas to be examined, and absorbs therefrom selected components if such are present. In the second position the device is in the flow of gas in a closed cycle so that the sorbed gas is desorbed and conducted to a detecting device, after which it is returned through desiccant, filter, heating, or other appropriate means. By suitable selection of sorption and desorption temperatures and sorptive materials, sensitivity and specificity may be enhanced.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described certain preferred embodiments of the invention.

BRIEF DESCRIPTION OF THE DRAWING

In the drawing, in which like reference numerals identify corresponding parts throughout the several views.

DETAILED DESCRIPTION OF THE PREFERRED EMBODIMENT

Figure 1:
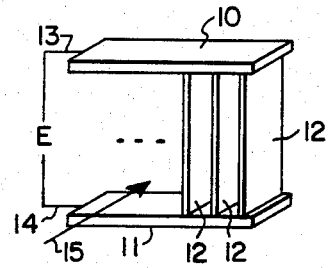
FIG. 1 is a schematic showing of the general operation of the invention.

The principle of the invention is best shown in FIG. 1. Here the sorption-desorption device is shown to comprise a pair of plates 10 and 11 which mount a plurality of spaced thin fins 12. Plates 10 and 11 are of electrically conductive material, such as metal, and are connected to the terminals 13 and 14 of a source of electrical energy. Fins 12 have relatively high electrical resistance, so that when a current flows through them between plates 10 and 11 their temperature rises. The fins are made of or are coated with sorptive material, so that when they are at low temperature they sorb material from the air flowing across them in the direction of the arrow 15, and when they are heated the sorbed material is desorbed.

Figure 2:
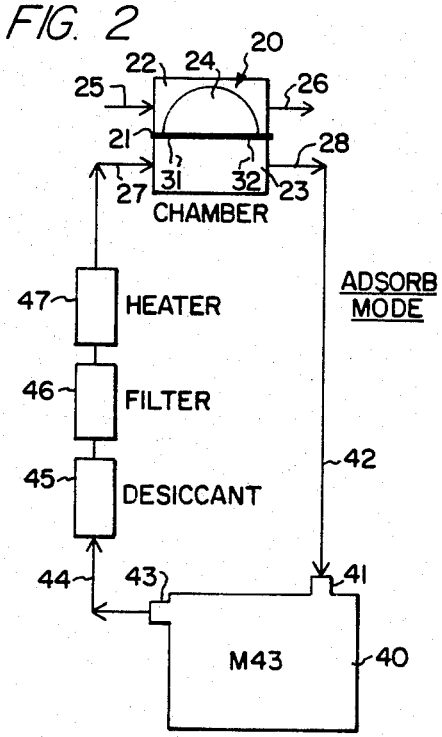
FIGS. 2 and 3 show the device in sorption and desorption modes, in cooperation with a chemical agent detector.
Figure 3:
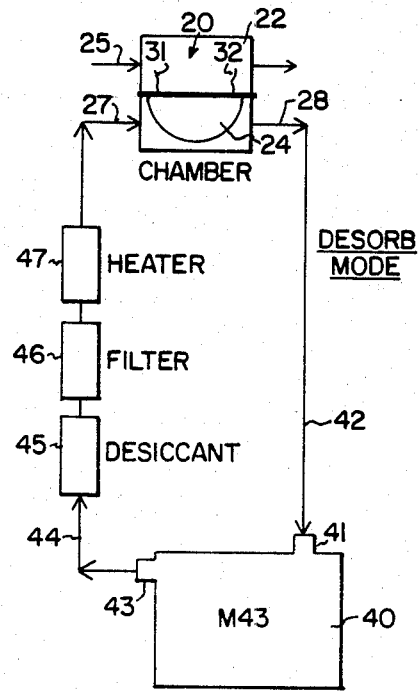

FIGS. 2 and 3 show the invention applied to increasing the sensitivity or specificity of a known chemical agent detector. Here a housing 20 is divided by a partition 21 into a sorption chamber 22 and a desorption chamber 23. An assembly of fins 24 is mounted to pivot in an aperture in partition 21, so that the fins may be located either in chamber 22 or in chamber 23. Except when the fins are being pivoted, the assembly occludes the opening in the partition. Chamber 22 has an inlet 25 and an outlet 26, and chamber 23 has an inlet 27 and an outlet 28. The air to be analyzed is drawn through chamber 22 from inlet 25 to outlet 26 by suitable means not shown. Electrical energy for heating the fins may be supplied on a set of flex leads 31 and 32. Alternately, the two pivot pins (not shown) of the fin assembly can also serve as electrical connectors.

A chemical agent detector 40, such as the U.S. Army M43, has its inlet 41 connected by a conduit 42 to outlet 28, and draws air from chamber 23, returning it to the chamber through outlet 43 and a conduit 44 which includes a desiccant 45 and a filter 46, leading to inlet 27 of chamber 23. Instead of directly heating the sorption fins, the return air can be heated by a heater 47.

FIG. 2 shows that in the sorption condition of the device fins 24 are in chamber 22, so that contaminants in the air flowing through chamber 22 are sorbed on fins 24, which at that time are not being heated. After an appropriate interval, fins 2 are pivoted out of chamber 22 into chamber 23 (see FIG. 3). Heat is applied, either electrically through conductors 31 and 32, or by operation of heater 47: the contaminants sorbed on fins 24 are now desorbed and supplied to detector 40.

One advantage of this arrangement is that by appropriate selection of the sorptive material at fins 24, and the sorption and desorption temperatures, the sensitivity or specificity of the overall system may be considerably increased.

Figure 4:
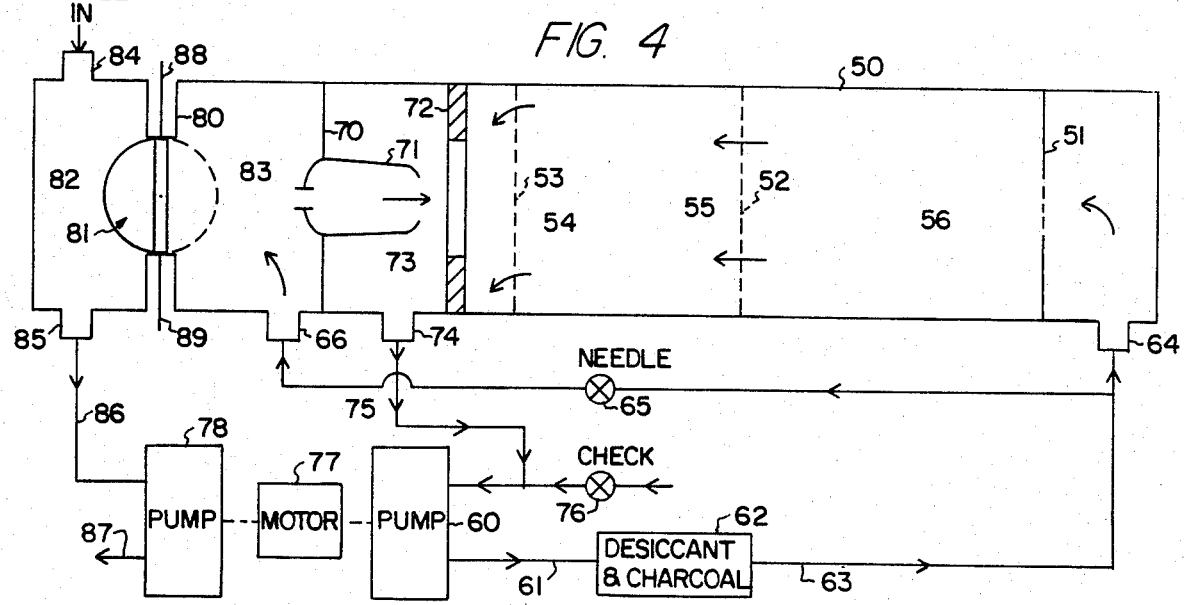
FIG. 4 shows a further embodiment of the invention including an ionization type of detection device.

FIG. 4 shows the invention in use with a drift tube detector. Here a housing 50 encloses a drift tube of the type shown in Castleman et al. U.S. Pat. No. 4,238,678, which includes a collector 51 and a pair of grids 52 and 53, as well as a plurality of guard rings, not shown, 24 all electrically energized, as taught in the patent, from a suitable voltage source, not shown, to provide a first drift region 54, a combining region 55, and a second drift region 56. A pump 60 supplies air to housing 50 through conduit 61, a desiccant and a gas purifier such as charcoal bed 62, and conduit 63 to a first inlet 64, and further through a needle valve 65 to a second inlet 66. A partition 70 in housing 50 includes a restriction 71, and an annular ionization source 72 is provided in the ionization region 73 between restriction 71 and grid 53: air is withdrawn from housing 50 at an outlet 74 to return to pump 60 through conduit 75: additional air may be supplied as needed through a check valve 76.

Pump 60 is operated by a motor 77, which also drives a second pump 78. Housing 50 has a second partition 80 with an aperture in which there is pivotally mounted an assembly of fins 81 like assembly 24 of FIGS. 2 and 3. Partition 80 separates a sorption chamber 82 from a desorption chamber 83 located between the fin assembly and partition 70. Pump 78 draws air to be analyzed into chamber 82 through an inlet 84 and exhausts it through an outlet 85 and a conduit 86, discharging it at 87. Electrical energy for heating the fins may be supplied on flex leads 88 and 89.

The fit of the fin assembly in partition 80 is such that in either pivoted position of the assembly there is no appreciable air flow through the partition aperture in either direction.

OPERATION OF THE INVENTION

The structure of FIG. 4 operates as follows. With fins pivoted into chamber 82 as shown, operation of motor 77 causes pump 78 to draw air to be tested, at ambient temperature, across the fins 81. At this time no electrical energy is supplied on leads 88 and 89, and contaminants in the air are sorbed on the fins. At the same time pump 60 is drawing air out of tube 50 at output 74, passing it through desiccant and charcoal bed 62, and returning it to the tube at 64 and 66, thus sweeping the tube clear of any gas previously contained therein. An appropriate indicator connected to collector 51 may be calibrated for uncontaminated air.

After an appropriate interval, fin assembly 81 is pivoted out of chamber 82 and into chamber 83. If during this interval some air escapes from tube 50 through the aperture in partition 80, it can be made up through check valve 76. After the pivoting is completed, pump 78 simply draws sample air through empty chamber 82. However, flex leads 88 and 89 may now be energized to heat the fins, and the material sorbed thereon is desorbed into air drawn into the tube through inlet 66, passes through restriction 71, and mixes in counter-current with air entering the tube through inlet 64. Ionization is caused by ionizing source 72, and operation of the tube to indicate the presence of contaminant ions takes place as is described in connection with the Castleman et al. patent.

The arrangement has a number of advantages. In the first place, the tube basically operates only on clean air containing material desorbed from fins 81. By choosing appropriate fin material, the device may be made particularly sensitive to a selective contaminant although others may be present in the sample. In the second place, it is possible to desensitize the tube to some particular contaminant in the air, when this is desired, by using a sorbant which does not sorb that particular contaminant, so that although others may be present in the sample, they are not present in the desorbed material supplied by the fins in chamber 83.

Such material may be selected from the class including porous carbon, germanium, nickel, silicon, tantalum, tellurium, various oxides, borides, carbides, arsenides, antimonides, selenides, phosphides, tellurides, and sulfides. Conventional gas chromatography packing materials such as porous polymers, graphitized carbon blacks, molecular sieves and porous silica, can also be used.

One further advantage of the invention should be pointed out. If, after the device has been displaced into the desorption chamber, heat is supplied according to a time and temperature program, it is possible to desorb successive components in sequence, so that the presence, identity, and relative proportions of distinguishable components in the air being tested may be determined.

For example, suppose the sorption procedure to have continued at room temperature for a long enough time that any contaminant including ethane, methane, and sulfur dioxide, have been sorbed to a desired degree. If then the device is heated to a temperature of 50° C. and is held there for about 13 seconds, most of the sorbed methane will be desorbed without appreciable desorption of ethane or sulfur dioxide. If the temperature is then raised to 110° C. and held there for about 13 seconds, most of the ethane will be desorbed, and the sulfur dioxide will be desorbed in about 13 seconds if the temperature is raised to 200° C. By this procedure and analysis of the contaminant content of the air being tested can be accomplished.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

What is claimed is:

1. In combination:
   a housing defining sorption and desorption chambers separated by a partition having an aperture which is bilaterally symmetrical about an axis;
   and sorption means comprising a plate, pivotally mounted in said aperture for rotation about said axis through first and second positions in which it substantially occludes said aperture, and a plurality of generally semicircular, mutually spaced sorption wafers mounted on one face of said plate and generally orthogonal to said axis, so that in said first position of said plate said wafers are in said sorption chamber, while in said second position of said plate said wafers are in said desorption chamber.

2. The combination of claim 1 and means causing movement of said sorption means between said first and second positions of said plate.

3. The combination of claim 1 and means for supplying gas to be sampled to said sorption chamber and means for supplying gas from said desorption chamber to a gas analyzer.

4. In a gas analyzing system, in combination:
   a housing defining sorption and desorption chambers separated by a partition having an aperture which is bilaterally symmetrical about an axis, sorption means comprising a plate, pivotally mounted in said aperture for rotation about said axis through first and second positions in which it substantially occludes said aperture, and a plurality of generally semicircular mutually spaced sorption wafers mounted on one face of said plate and generally orthogonal to said axis, so that in said first position of said plate said wafers are in said sorption chamber, while in said second position of said plate said wafers are in said desorption chamber;
   means causing movement of said sorption means between said first and second positions of said plate;
   means supplying gas to be sampled to said sorption chamber;
   gas analyzing apparatus;
   and means causing circulation of gas in a closed path between said desorption chamber and said analyzing apparatus, said path including desiccant and absorbant means.

* * * * *